United States Patent
Sakaguchi et al.

(10) Patent No.: US 9,555,025 B2
(45) Date of Patent: Jan. 31, 2017

(54) OINTMENT WITH EXCELLENT FORMULATION STABILITY

(75) Inventors: Tomoki Sakaguchi, Kyoto (JP); Hidetoshi Emi, Kyoto (JP)

(73) Assignees: Maruho Co., Ltd., Osaka-shi, Osaka (JP); Mitsubishi Tanabe Pharma Corporation, Osaka-shi, Osaka (JP)

( * ) Notice: Subject to any disclaimer, the term of this patent is extended or adjusted under 35 U.S.C. 154(b) by 42 days.

(21) Appl. No.: 14/008,413

(22) PCT Filed: Mar. 28, 2012

(86) PCT No.: PCT/JP2012/058072
§ 371 (c)(1),
(2), (4) Date: Sep. 27, 2013

(87) PCT Pub. No.: WO2012/133492
PCT Pub. Date: Oct. 4, 2012

(65) Prior Publication Data
US 2014/0018387 A1      Jan. 16, 2014

(30) Foreign Application Priority Data
Mar. 31, 2011 (JP) ................................. 2011-080154

(51) Int. Cl.
| | |
|---|---|
| *A61K 31/4709* | (2006.01) |
| *A61K 9/00* | (2006.01) |
| *A61K 47/10* | (2006.01) |
| *A61K 47/12* | (2006.01) |
| *A61K 47/14* | (2006.01) |
| *A61K 47/18* | (2006.01) |
| *A61K 47/22* | (2006.01) |

(52) U.S. Cl.
CPC ......... *A61K 31/4709* (2013.01); *A61K 9/0014* (2013.01); *A61K 47/10* (2013.01); *A61K 47/12* (2013.01); *A61K 47/14* (2013.01); *A61K 47/18* (2013.01); *A61K 47/22* (2013.01)

(58) Field of Classification Search
CPC ...... A61K 9/0014; A61K 47/10; A61K 47/12; A61K 47/14; A61K 47/18; A61K 47/22; A61K 31/4709
USPC ....................................................... 514/312
See application file for complete search history.

(56) References Cited

U.S. PATENT DOCUMENTS 5,795,916 A * 8/1998 Sekine et al. .................. 514/567
7,868,019 B2 * 1/2011 Naotsuka et al. ............. 514/307
2003/0144300 A1 * 7/2003 Magee et al. .................. 514/256
2005/0158371 A1 * 7/2005 Nishikado et al. ............ 424/449
2009/0069307 A1 * 3/2009 Takagi et al. ............... 514/224.2

FOREIGN PATENT DOCUMENTS

| JP | A-03-118323 | 5/1991 |
| JP | A-09-059255 | 3/1997 |
| JP | A-09-169637 | 6/1997 |
| JP | A-10-226647 | 8/1998 |
| JP | A-2006-151964 | 6/2006 |
| WO | WO 2007/043426 JP | 4/2007 |

OTHER PUBLICATIONS

International Search Report, PCT/JP2012/058072 (May 29, 2012), English language translation (1 page).*
International Preliminary Report on Patentability, PCT/JP2012/058072 (Oct. 8, 2013), English language translation (8 pages).*
Monzir-Pal, Characteristics of Surfactants and Emulsions, [Retrieved from internet <URL: http://www.monzir-pal.net/Industrial/Characteristics%20of%20Surfactants%20and%20Emulsions.htm >], [Downloaded Jul. 26, 2015], 8 pages.*
Krishna et al., Improving emulsification efficacy of lecithin by formulation design. I: Effect of adding a secondary surfactant; PDA J Pharm Sci Technol., Nov.-Dec. 1998; 52(6):331-6; Abs. only (2 pages).*
Remington's Pharmaceutical Sciences, 17th ed., Algonso R. Gennaro, ed.( 1985), pp. 1301-1306 (Chapter 68, Pharmaceutical Necessities, excerpt on Ointment Bases) and pp. 1567-1584 (Chapter 88, Medicated Applications), total 32 pages including cover, title page, contents.*
USP, Ueda et al., The Topical/Transdermal Ad Hoc Advisory Panel for the USP Performance Tests of Topical and Transdermal Dosage Forms, Clarence T. Ueda (Chair), Stimuli to the Revision Process, USP (United States Pharmacopeia) Pharmacopeia Forum, vol. 35 (3): 750-764 (May-Jun. 2009), 15 pages.*
(URL for USP citation above: [Retrieved from internet <URL: http://www.usp.org/sites/default/files/usp_pdf/EN/USPNF/transdermalStimArticle.pdf >]).*

* cited by examiner

*Primary Examiner* — Miriam A Levin
(74) *Attorney, Agent, or Firm* — Muncy, Geissler, Olds & Lowe, P.C.

(57) ABSTRACT

Provided is an ointment which has excellent drug stability and excellent drug uniformity. The ointment, which comprises 1 to 5% by weight of 1-[2-[(4S)-4-hydroxy-1,2,3,4-tetrahydroquinolin-1-yl]-4-pyridyl]-2,3-bis(hydroxymethyl)-6,7-dimethoxynaphthalene·3/2 hydrate, 3 to 7% by weight of a separation inhibitor, 15 to 50% by weight of a hydrocarbon gel, a pH controller and 0.05 to 0.4% by weight of an antioxidant, has excellent drug stability and excellent drug dispersibility. In the present ointment, polyoxyethylene (196) polyoxypropylene (67) glycol is preferred as the separation inhibitor, diisopropanolamine is preferred as the pH controller, and dibutylhydroxytoluene is preferred as the antioxidant.

6 Claims, No Drawings

OINTMENT WITH EXCELLENT FORMULATION STABILITY

This application is a national stage of International Application No.: PCT/JP2012/058072, which was filed on Mar. 28, 2012, and which claims priority to JP2011-080154, which was filed on Mar. 31, 2011, and which are both herein incorporated by reference.

TECHNICAL FIELD

The present invention relates to an ointment with excellent formulation stability, in particular, an ointment which can stably keep a naphthalene derivative useful as a PDE4 inhibitor, is excellent in the uniformity of the drug in the formulation, and further has a hardness suitable for application, and physical stability.

BACKGROUND ART

Hitherto, as ah active ingredient having a PDE4 inhibitory effect, reports have been made about naphthalene derivatives each having a specific chemical structure. Known have also been medical compositions for preventing or treating asthma, therapeutic agents for dermatitis, and therapeutic agents for skin, injury that each make use of advantageous effects of any one of the derivatives (for example, Patent Literatures 1 to 4 listed below).

However, such an active ingredient is a drug that does not easily ensure the stability of a formulation thereof. As a solving solution for ensuring the uniformity or bleeding of the drug in an ointment, a method of increasing the hardness of the formulation is easily conceivable. In this case, however, a problem is caused that it s difficult to apply the ointment.

PRIOR ART DOCUMENTS

Patent Literatures

Patent Literature 1: JP-A-09-59255
Patent Literature 2: JP-A-10-226647
Patent Literature 3: WO 2007/043426
Patent Literature 4: JP-A-2006-151964

SUMMARY OF THE INVENTION

Problems to be Solved by the Invention

An object of the present invention is to overcome the above-mentioned problems in the prior art, and provide an ointment which can stably keep a drug having a PDE4 inhibitory effect, is excellent in the uniformity of the drug in the formulation, and further has a hardness suitable for application and physical stability (such as bleeding).

The present inventors have made various investigations to find out that an appropriate pH controller, an antioxidant, a base and a separation inhibitor are selected and the selected ingredients are blended with each other, whereby the resultant can attain the stability of a drug having a PDE4 inhibitory effect and the uniformity of the drug, restrain bleeding thereof, and more a formulation hardness suitable for application. Thus, the present invention has been accomplished.

Means for Solving the Problems

In the ointment of the present invention that can solve the above-mentioned problems, the following are blended with each other: a separation inhibitor selected from the group consisting of polyoxyethylene (196) polyoxypropylene (67) glycol, cetostearyl alcohol, behenyl alcohol, cetyl palmitate, polyoxyethylene (160) polyoxypropylene (30) glycol, and polyoxyethylene (54) polyoxypropylene (39) glycol; and a hydrocarbon gel as a base. In this way, the ointment attains excellent drug stability and drug uniformity. This ointment characterized in that it contains: 1 to 5% by weight of 1-[2-[(4S)-4-hydroxy-1,2,3,4-tetrahydroquinoline-1-yl]-4-pyridyl]-2,3-bis(hydroxymethyl)-6,7-dimethoxynaphthalene·3/2 hydrate, 3 to 7% by weight of one or more separation inhibitor selected from the group consisting of polyoxyethylene (196) polyoxypropylene (67) glycol, cetostearyl alcohol, behenyl alcohol, cetyl palmitate, polyoxyethylene (160) polyoxypropylene (30) glycol, and polyoxyethylene (54) polyoxypropylene (39) glycol, 15 to 50% by weight of a hydrocarbon gel, a pH controller selected from the group consisting of diisopropanolamine, citric acid monohydrate, lactic acid, triisopropanolamine, triethanolamine, and monoethanolamine, and 0.05 to 0.4% by weight of an antioxidant selected from the group consisting of dibutylhydroxytoluene, butylhydroxyanisole, propyl gallate, tocopherol, and pentaerythrityl-tetrakis[3-(3,5-di-t-butyl-4-hydroxyphenyl)propionate].

The present invention also relates to the ointment which is characterized in that the separation inhibitor is polyoxyethylene (196) polyoxypropylene (67) glycol, the pH controller is diisopropanolamine, and the antioxidant is dibutylhydroxytoluene.

The present invention also relates to the ointment which is characterized in that it further contains at least 3% by weight of 1,3-butylene glycol.

Effects of the Invention

The present invention makes it possible to provide a pharmaceutical preparation (ointment) containing a drug having PDE4 inhibitory effect, which is a pharmaceutical preparation that has not easily ensured formulation stability so far, and ensure a quality required for a medicament.

MODE FOR CARRYING OUT THE INVENTION

Hereinafter, a description will be made about each of the ingredients contained in the ointment of the present invention.

An active ingredient in the present invention is one of naphthalene derivatives known as a drug having a PDE4 inhibitory effect, i.e., 1-[2-[(4S)-4-hydroxy-1,2,3,4-tetrahydroquinoline-1-yl]-4-pyridyl]-2,3-bis(hydroxymethyl)-6,7-dimethoxynaphthalene·3/2 hydrate. This compound (molecular formula: $C_{28}H_{28}N_2O_5 \cdot 3/2H_2O$) has the following structural formula:

[Chemical formula 1]

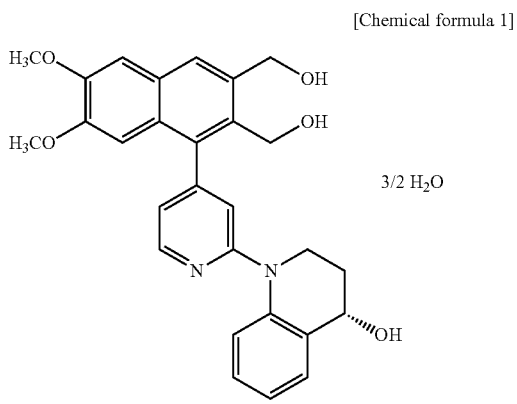 [SMILES: COc1cc2cc(CO)c(CO)c(-c3ccnc(N4CC[C@H](O)c5ccccc54)c3)c2cc1OC]

3/2 H₂O

In the ointment of the present invention, the blending amount of the drug is from 1 to 5% by weight, more preferably from 1.25 to 5% by weight. If the amount shows a low concentration of less than 1% by weight, it is difficult to ensure the stability and dispersibility of the drug. Reversely, if the amount shows a concentration of more than 5% by weight, the drug is unfavorably precipitated.

About the active ingredient blended as a separation inhibitor in the ointment of the present invention, i.e., polyoxyethylene (196) polyoxypropylene (67) glycol, cetostearyl alcohol; behenyl alcohol, cetyl palmitate, polyoxyethylene (160) polyoxypropylene (30) glycol, or polyoxyethylene (54) polyoxypropylene (39) glycol, the blending amount thereof is from 3 to 7% by weight. If the blending amount is less than 3% by weight, it is difficult to ensure the drug uniformity. Reversely, if the blending amount is more than 7% by weight, the formulation unfavorably becomes high in the hardness not to be easily applied, and is further lowered in adhesive property. In the present invention, it is possible to use, as polyoxyethylene (196) polyoxypropylene (67) glycol, a commercially available product, for example, UNI-LUB 70DP-950B (trade name) manufactured by NOF CORPORATION. This compound, polyoxyethylene (196) polyoxypropylene (67) glycol, is a compound that is also named as polyoxyethylene (200) glycol polyoxypropylene (70). It is possible to use, as polyoxyethylene (160) polyoxypropylene (30) glycol, a commercially available product, for example, ADEKA PLURONIC F-68 (trade name) manufactured by ADEKA CORPORATION, and use, as polyoxyethylene (54) polyoxypropylene (39) glycol, a commercially available product, for example, ADEKA PLURONIC P-85 (trade name) manufactured by ADEKA CORPORATION.

In the present invention, the hydrocarbon gel is an ingredient used as a base of an ointment for external application, and for example, PLASTIBASE (registered trade name) and the like can be used. The blending amount of the hydrocarbon gel is from 15 to 50% by weight. If the blending amount is less than 15% by weight, it is difficult to ensure the quality of the formulation from the viewpoint of the drug uniformity and bleeding. Reversely, if the blending amount is more than 50% by weight, the formulation unfavorably becomes high in the hardness not to be easily applied.

About the ingredient blended as a pH controller in the ointment of the present invention, i.e., diisopropanolamine (DIPA), citric acid monohydrate, lactic acid, triisopropanolamine, triethanolamine, or monoethanolamine, the blending amount thereof needs only to be an amount permitting the pH of a drug phase of the ointment to be adjusted in the range of 8 to 10.5. The drug phase referred to herein denotes a solution of a homogenous monophasic system in which the drug, the pH controller and the antioxidant are dissolved in an aqueous base (such as 1,3-butylene glycol). The pH of the drug phase is a value obtained by measuring the pH of the drug phase. When DIPA is used as the pH controller, the blending amount thereof is from 0.04 to 5% by weight. If the blending amount is less than 0.04% by weight, the drug is had in stability so that from a time just after the preparation thereof, a degradation product is generated. Reversely, if the blending amount is more than 5% by weight (the upper limit amount in precedents in each of which the controller is used in an ordinary external formulation), the amount exceeds a usable concentration thereof in any ordinary external formulation. Thus, unfavorably, it has not yet been verified at present that the amount attains the retention of safety.

About the ingredient blended as an antioxidant, (stabilizer) in the ointment of the present invention, i.e., dibutylhydroxytoluene (BHT), butylhydroxyanisole (BHA), propyl gallate, tocopherol, or pentaerythrityl-tetrakis[3-(3,5-di-t-butyl-4-hydroxyphenyl)propionate], the blending amount is from 0.05 to 0.4% by weight. If the blending amount is less than 0.05% by weight, the stability of the drug is bad so that a degradation product is produced. When BHT is used as the antioxidant, it is not appropriate that BHT is added to a medicament in an unnecessarily large amount. Thus, an optimal range of the amount thereof is the range stated herein.

In the present invention, it is allowable to incorporate 1,3-butylene glycol as a dissolving agent, besides the above-mentioned ingredients, in an amount of at least 3% by weight, preferably an amount of 3 to 20% by weight. It is also allowable to incorporate, into the ointment of the present invention, white beeswax or stearyl alcohol as a base other than the hydrocarbon gel, or incorporate thereinto vaseline (preferably, white vaseline) to adjust the amount of the whole into 100% by weight.

The ointment formulation of the present invention may be produced in accordance with a conventional method for producing an ointment. For example, a desired ointment formulation can be obtained by (1) uniformy admixing the base ingredients (a hydrocarbon gel, white vaseline, white beeswax and stearyl alcohol); and a separation inhibitor (such as polyoxyethylene (196) polyoxypropylene (67) glycol) to prepare an oil phase, followed by (2) admiring a drug, a dissolving agent (such as 1,3-butylene glycol), a pH controller (such as diisopropanolamine or citric acid monohydrate) and an antioxidant (such as dibutylhydroxytoluene) to the oil phase under heating and stirring.

Hereinafter, working examples of the ointment formulation of the present invention will be demonstrated.

Meanwhile, each ointment formulation of Comparative Example 6 and 7, for reference, was produced by using microcrystalline wax or ceresin instead of the hydrocarbon gel. Each ointment formulation of Comparative Example 12, 13, 14, 15 and 16 was produced by using, instead of polyoxyethylene (196) polyoxypropylene (67) glycol, polyoxyethylene glycol monostearate, sorbitan monostearate, glycerin monostearate, stearic acid, or a saccharose aliphatic acid ester.

EXAMPLES

1. Comparative Test-about Drug Stability

Ointments (Examples 1 to 6 and Comparative Examples 1 and 2) each having a composition shown in Table 1 described below were prepared. The stability of the drug was evaluated by measuring the amount of a resultant degradation product at each of the time of the preparation (initial time) and respective times after stored at 40° C. and 75% RH for one month, after stored at 40° C. and 75% RH for three months and after stored at 60° C. for four weeks. About a judgment criterion (index for quality-securement) of the stability, any one of the ointments was judged to be "good in drug stability" in the case where the percentage of the degradation product was 0.1% or less after the storage at 40° C. and 75% RH for the three months, that was 0.1% or less after the storage at 60° C. for the two weeks, or that was 0.2% or less after the storage at 60° C. for the four weeks.

In this comparative test, the used "hydrocarbon gel" was a commercially available product, "PLASTIBASE" (manufactured by Bristol-Myers Company), and the used "polyoxyethylene (196) polyoxypropylene (67) glycol (separation inhibitor)" was a commercially available product, "UNILUB 70DP-950B" (NOF CORPORATION). The blending amount of citric acid monohydrate was set to 0.02% by weight; that of white beeswax to 5% by weight; and that of stearyl alcohol to 5% by weight. The blending amount of white vaseline was adjusted to set the amount of the whole to 100% by weight.

formulation incapable of ensuring drug stability. By contrast, the ointments of Examples 1 to 6, which each contained DIPA in a proportion of 0.04% by weight, 0.8% by weight or 5% by weight, were each good in drug stability. The pH of the drug phase of each of Examples 1 to 6 ranged from 8 to 10.5.

2. Comparative Tests about Drug Uniformity, Formulation Hardness and Bleeding

Ointments (Examples 1, 7 and 8, and Comparative Examples 3 to 5) each having a composition shown in Table 2 described below were prepared. The ointments were compared with each other about drug uniformity, formulation hardness and bleeding that were based on a difference in the blending amount of the hydrocarbon gel. These three evaluating items are items for evaluating the respective qualities of the formulations. The hardness and the bleeding, out of the three, are evaluations connected to use feeling.

About the drug uniformity in Table 2, the following was used as a judgment criterion for a good uniformity: the relative standard deviation of the content by percentage is 3% or less at the time of the preparation (initial time), and in the evaluation with time (after one month or two months at 40° C.) the standard deviation, is 6% or less. The relative

TABLE 1

| Ingredient | | Exam. 1 | Exam. 2 | Comp. Exam. 1 | Exam. 3 | Exam. 4 | Comp. Exam. 2 | Exam. 5 | Exam. 6 |
|---|---|---|---|---|---|---|---|---|---|
| Drug | | 1.25 | 5 | 1.25 | 1.25 | 1.25 | 1.25 | 1.25 | 1.25 |
| 1,3-BG | | 15 | 15 | 15 | 15 | 15 | 15 | 15 | 15 |
| BHT | | 0.2 | 0.2 | — | 0.05 | 0.4 | 0.2 | 0.2 | 0.2 |
| DIPA | | 0.8 | 0.8 | 0.8 | 0.8 | 0.8 | — | 0.04 | 5 |
| UNILUB | | 5 | 5 | 5 | 5 | 5 | 5 | 5 | 5 |
| Hydrocarbon gel | | 25 | 25 | 25 | 25 | 25 | 25 | 25 | 25 |
| Other common ingredients | | Citric acid monohydrate, White beeswax, Stearyl alcohol, White Vaseline | | | | | | | |
| Amount of | Initial | 0 | 0 | 0 | 0 | 0 | 2.56 | 0 | 0 |
| degradation | 40° C. · 1M | 0.05 | 0.05 | 0.15 | 0.09 | 0.05 | — | 0.04 | 0.07 |
| product | 40° C. · 3M | 0.06 | 0.05 | 0.19 | 0.10 | 0.07 | — | 0.10 | — |
| (%) | 60° C. · 4 W | 0.07 | 0.08 | — | — | — | — | — | 0.07 |

As shown as the test results in Table 1, about the ointment of Comparative Example 1, which contained no BHT, the amount of the degradation product was 0.15% after the storage at 40° C. and 75% RH for the one month, and that was 0.19% after the storage at 40° C. and 75% RH for the three months. Thus, the ointment was a formulation incapable of ensuring drug stability. By contrast, the ointments of Examples 1 to 6, which each contained BHT in a proportion of 0.05% by weight, 0.2% by weight or 0.4% by weight, were each good in drug stability.

Similarly, about the ointment of Comparative Example 2, which contained no DIPA, a degradation product, was already produced from the initial time (just after the preparation). It has been understood that this example was a standard deviation of the content by percentage is a value obtained by collecting respective samples from the upper, middle and lower regions of the storing-container, and presenting a relative standard deviation of the respective contents by percentage in the samples. About the formulation hardness, a penetrometer was used to measure the penetration degree of each of the formulations at 25° C., and the degree was compared with that of a commercially available ordinary external formulation. As a standard of the quality, the following was used: the formulation was not poorer in the degree than the commercially available preparation. When the degree was 6.0 mm or more, the formulation was judged to be good. About the bleeding, any one of the formulations was judged to be "good" when the value thereabout, was 5% or less.

TABLE 2

| Ingredient | | Comp. Exam. 3 | Comp. Exam. 4 | Exam. 7 | Exam. 1 | Exam. 8 | Comp. Exam. 5 |
|---|---|---|---|---|---|---|---|
| Drug | | 1.25 | 1.25 | 1.25 | 1.25 | 1.25 | 1.25 |
| 1,3-BG | | 15 | 15 | 15 | 15 | 15 | 15 |
| BHT | | 0.2 | 0.2 | 0.2 | 0.2 | 0.2 | 0.2 |
| DIPA | | 0.8 | 0.8 | 0.8 | 0.8 | 0.8 | 0.8 |
| UNILUB | | 5 | 5 | 5 | 5 | 5 | 5 |
| Hydrocarbon gel | | — | 5 | 15 | 25 | 50 | 64 |
| Other common ingredients | | Citric acid monohydrate, White beeswax, Stearyl alcohol, White Vaseline | | | | | |
| Relative standard | Initial | 0.6 | 0.6 | 1.0 | 0.6 | 0.4 | — |
| deviation of the | 40° C. · 1M | 7.7 | 8.2 | 1.3 | 1.4 | 0.5 | — |
| content (%) | 40° C. · 2M | — | — | 5.2 | 2.6 | 1.9 | — |

TABLE 2-continued

| Ingredient | | Comp. Exam. 3 | Comp. Exam. 4 | Exam. 7 | Exam. 1 | Exam. 8 | Comp. Exam. 5 |
|---|---|---|---|---|---|---|---|
| Penetration degree (mm) | Initial | 10.0 | 10.1 | 7.6 | 7.1 | 6.0 | 5.5 |
| Bleeding (%) | 30° C. · 2M | 7.7 | 6.5 | 3.4 | 1.8 | 2.3 | — |

As shown as results of the test in Table 2, the case where no hydrocarbon gel was added (Comparative Example 3), and the case where the hydrocarbon gel was added in a proportion of 5% by weight (Comparative Example 4) were out of the standard values about each of the drug uniformity and the bleeding, not to succeed in ensuring a quality for an external formulation. By contrast, the cases where the hydrocarbon gel was added in a proportion of 15 to 50% by weight (Examples 1, 7 and 8) each gained respective excellent values about the drug uniformity, the hardness and the bleeding, so as to be identified as a formulation capable of ensuring a quality for an external formulation. However, about the ointment wherein the hydrocarbon gel was added in a proportion of 64% by weight (Comparative Example 5), the proportion being approximately a maximum addable proportion, the hardness was less than the standard value (penetration degree: less than 6.0 mm). Thus, it has been understood that in connection with use feeling, this ointment was not easily applied, so as to be unsuitable for a formulation.

Subsequently, ointments having a composition shown in Tables 3 and 4 were prepared. Evaluations were made about physical properties of the formulations obtained in the case of using microcrystalline or ceresin, which is a base of a saturated hydrocarbon other than hydrocarbon gels (see Table 3). An investigation was also made about an optimal blending amount of polyoxyethylene (196) polyoxypropylene (67) glycol added as the separation inhibitor (see Table 4). About the adhesive property of each of the formulations, a rheometer was used to measure the formulation at 25° C., and the resultant adhesive property was compared with that of a commercially available ordinary external formulation. As a standard of the quality, the following was used: the formulation was not poorer in the property than the commercially preparation. When the measured value was 10.0 mJ or less, the formulation was judged to be "good".

TABLE 3

| Ingredient | | Example 2 | Comp. Exam. 6 | Comp. Exam. 7 |
|---|---|---|---|---|
| Drug | | 5 | 5 | 5 |
| 1,3-BG | | 15 | 15 | 15 |
| BHT | | 0.2 | 0.2 | 0.2 |
| DIPA | | 0.8 | 0.8 | 0.8 |
| UNILUB | | 5 | 5 | 5 |
| Hydrocarbon gel | | 25 | — | — |
| Microcrystalline wax | | — | 25 | — |
| Ceresin | | — | — | 25 |
| Other common ingredients | | Citric acid monohydrate, White beeswax, Stearyl alcohol, White waseline | | |
| Relative standard deviation of the content (%) | Initial | 0.4 | — | — |
| | 40° C. · 1M | 0.5 | — | — |
| | 40° C. · 2M | 1.9 | — | — |
| Penetration degree (mm) | Initial | 8.1 | 4.4 | 3.5 |
| Bleeding (%) | 30° C. · 2M | 2.1 | 0.3 | 0.0 |
| Adhesive property (mJ) | Initial | 5.7 | — | — |

TABLE 4

| Ingredient | | Exam. 2 | Comp. Exam. 8 | Exam. 9 | Exam. 10 | Comp. Exam. 9 | Comp. Exam. 10 | Comp. Exam. 11 |
|---|---|---|---|---|---|---|---|---|
| Drug | | 5 | 5 | 5 | 5 | 5 | 5 | 5 |
| 1,3-BG | | 15 | 15 | 15 | 15 | 15 | 15 | 15 |
| BHT | | 0.2 | 0.2 | 0.2 | 0.2 | 0.2 | 0.2 | 0.2 |
| DIPA | | 0.8 | 0.8 | 0.8 | 0.8 | 0.8 | 0.8 | 0.8 |
| UNILUB | | 5 | 2 | 3 | 7 | 8 | 14 | 30 |
| Hydrocarbon gel | | 25 | 25 | 25 | 25 | 25 | 25 | 25 |
| Other common ingredients | | Citric acid monohydrate, White beeswax, Stearyl alcohol, White waseline | | | | | | |
| Relative standard deviation of the content (%) | Initial | 0.4 | 0.1 | 0.5 | 0.4 | 0.1 | 0.1 | — |
| | 40° C. · 1M | 0.5 | 2.2 | 1.0 | 1.8 | 4.2 | 6.9 | — |
| | 40° C. · 2M | 1.9 | 9.5 | 2.7 | 2.4 | 2.1 | — | — |
| Penetration degree (mm) | Initial | 8.1 | 7.4 | 6.7 | 6.0 | 5.0 | 4.3 | 3.8 |
| Bleeding (%) | 30° C. · 2M | 2.1 | — | 1.9 | 1.4 | — | — | — |
| Adhesive property (mJ) | Initial | 5.7 | 6.0 | 6.9 | 7.9 | 11.1 | 14.1 | 31.3 |

As a result, about the cases of using microcrystalline wax or ceresin (Comparative Examples 6 and 7), the hardness thereof was out of the standard values. Thus, it has been understood that these formulations were very hard formulations. From this result, it has been determined that the use of these bases does not give any formulation good in use feeling.

About the blending amount of polyoxyethylene (196) polyoxypropylene (67) glycol added as the separation inhibitor, the blending wherein the amount was a proportion of 2% by weight did not give any problem to the formulations shout a formulation hardness nor adhesive property, thus, appropriate values were shown about these properties. However, this case failed to ensure drug uniformity (Comparative Example 8). When the blending amount of polyoxyethylene (196) polyoxypropylene (67) glycol was 8% or more by weight (Comparative Examples 9 to 11), the hardness and the adhesive property of the formulations were out of the judgment criteria so that these examples tended to be deteriorated in use feeling. By contrast, the ointments of the present invention (Examples 2, 9 and 10) each gained respective excellent values about the drug uniformity, the hardness and the bleeding, so as to be identified as a formulation capable of ensuring a quality for a external formulation. From these results, it has been determined that the optimal blending amount of polyoxyethylene (196) polyoxypropylene (67) glycol ranges from 3 to 7% by weight.

3. Comparative Tests about Drug Stability and Uniformity

Investigations were made about formulations in each of which the separation inhibitor blended in the ointments was changed from polyoxyethylene (196) polyoxypropylene (67) glycol to a different compound. Compounds each investigated as the separation inhibitor were monostearic acid ester type surfactants, a higher aliphatic acid compound, and a saccharose aliphatic acid ester described in Table 5.

TABLE 5

| Ingredient | | Exam. 1 | Comp. Exam. 12 | Comp. Exam. 13 | Comp. Exam. 14 | Comp. Exam. 15 | Comp. Exam. 16 |
|---|---|---|---|---|---|---|---|
| Drug | | 1.25 | 1.25 | 1.25 | 1.25 | 1.25 | 1.25 |
| 1,3-BG | | 15 | 15 | 15 | 15 | 15 | 15 |
| BHT | | 0.2 | 0.2 | 0.2 | 0.2 | 0.2 | 0.2 |
| DIPA | | 0.8 | 0.8 | 0.8 | 0.8 | 0.8 | 0.8 |
| UNILUB | | 5 | — | — | — | — | — |
| Monostearic acid Polyoxyethylene glycol | | — | 5 | — | — | — | — |
| Sorbitan monostearate | | — | — | 5 | — | — | — |
| Glyceryl monostearate | | — | — | — | 5 | — | — |
| Stearic acid | | — | — | — | — | 5 | — |
| Sucrose fatty acid ester | | — | — | — | — | — | 5 |
| Hydrocarbon gel | | 25 | 25 | 5 | 25 | 25 | 25 |
| Other common ingredients | | Citric acid monohydrate, White beeswax, Stearyl alcohol, White waseline | | | | | |
| Relative standard deviation of the content (%) | Initial | 0.6 | 0.5 | 0.6 | 0.5 | — | 0.3 |
| | 40° C. · 1M | 1.4 | 0.7 | 0.6 | 0.3 | — | 0.5 |
| | 40° C. · 2M | 2.6 | 2.5 | — | — | — | 1.5 |
| Amount of degradation product (%) | Initial | 0 | 0 | 0 | 0 | 0 | 0 |
| | 60° C. · 2 W | 0.07 | 0.27 | 0.43 | 0.20 | 1.32 | 0.20 |

As shown in Table 5, in the cases (Comparative Examples 12 to 16) of blending the monostearic acid ester type surfactants, the higher aliphatic acid compound, and the saccharose aliphatic acid ester, respectively, it was verified that these ointments might ensure drug uniformity. However, the ointments did not succeed in ensuring drug stability. Specifically, about the stability, the respective produced amounts of the resultant individual degradation products were estimated. As a result, in Comparative Examples 12 to 16, the amounts were each more than 0.1% at 60° C. after the two weeks. Thus, it has been understood that these ointments were formulations incapable of ensuring drug stability.

4. Hardness Comparison with Commercially Available Ointments

A comparison was made about the hardness between each commercially available ordinary external formulation, and the ointments of the present invention which had the respective compositions of Examples 1 and 2. Results measured therein are shown in Table 6 described below. The method of the measurement was the same as described above.

TABLE 6

| Name of formulation | Penetration degree (mm) |
|---|---|
| Example 1 | 7.1 |
| Example 2 | 8.1 |
| Protopic Ointment 0.1% | 7.9 |
| Antebate Ointment 0.1% | 9.0 |
| Nerisona Ointment 0.1% | 7.1 |
| Dermovate Ointment 0.05% | 9.4 |
| Locoid Ointment | 6.8 |
| Anderm Ointment 5% | 9.1 |

From the measurement results in Table 6, it has been understood that the ointments of the present invention which had the respective compositions of Examples 1 and 2 had a hardness suitable for application in the same manner as the commercially available ordinary external formulations.

5. Adhesive Property Comparison with Commercially Available Ointments

A comparison was made about adhesive property between each commercially available ordinary external formulation, and the ointment of the present invention which had the composition of Example 2. Results measured therein are shown in Table 7 described below. The method of the measurement was the same as described above.

TABLE 7

| Name of formulation | Measured value (mJ) |
|---|---|
| Example 2 | 5.7 |
| Antebate Ointment 0.1% | 5.4 |
| Nerisona Ointment 0.1% | 6.3 |
| Sawastin Ointment 0.1% | 3.2 |
| Dermovate Ointment 0.05% | 6.2 |
| Betnevate Ointment 0.12% | 4.2 |
| Locoid Ointment | 8.7 |
| Vesicum Ointment 5% | 4.1 |
| Andean Ointment 5% | 3.1 |

From the measurement results in Table 7, it has been verified that the ointment of the present invention which had the composition of Example 2 did not cause any problem about adhesive property, which is an index for estimating the tackiness of the formulation, in the same manner as the commercially available ordinary external formulations.

INDUSTRIAL APPLICABILITY

The ointment of the present invention is excellent in drug stability and uniformity in the formulation, and has a hardness suitable for application, and physical stability. Thus, according to the invention, the ointment makes it possible to ensure a quality required for a medicament.

The invention claimed is:

1. An ointment comprising:
   (i) an oil phase containing:
   3 to 7% by weight of a separation inhibitor selected from the group consisting of polyoxyethylene (196) polyoxypropylene (67) glycol, cetostearyl alcohol, behenyl alcohol, cetyl palmitate, polyoxyethylene (160) polyoxypropylene (30) glycol and polyoxyethylene (54) polyoxypropylene (39) glycol, and
   15 to 50% by weight of a hydrocarbon gel, and
   (ii) a drug phase being a homogenous solution in which 1 to 5% by weight of 1-[2-[(4S)-4-hydroxy-1,2,3,4-tetrahydroquinolin-1-yl]-4-pyridyl]-2,3-bis(hydroxymethyl)-6,7-dimethoxynaphthalene×3/2hydrate,
   diisopropanolamine as a pH controller, and
   0.05 to 0.4% by weight of an antioxidant selected from the group consisting of dibutylhydroxytoluene, butylhydroxyanisole, propyl gallate, tocopherol and pentaerythrityl-tetrakis[3-(3,5-di-t-butyl-4-hydroxyphenyl)propionate]
   are dissolved in an aqueous base,
   the pH of the drug phase being in the range of 8 to 10.5.

2. The ointment according to claim 1, wherein the separation inhibitor is polyoxyethylene (196) polyoxypropylene (67) glycol, and the antioxidant is dibutylhydroxytoluene.

3. The ointment according to claim 1, wherein the aqueous base is 1,3-butylene glycol.

4. The ointment according to claim 1, wherein the separation inhibitor is selected from the group consisting of polyoxyethylene (196) polyoxypropylene (67) glycol, cetostearyl alcohol, polyoxyethylene (160) polyoxypropylene (30) glycol and polyoxyethylene (54) polyoxypropylene (39) glycol.

5. The ointment according to claim 1, wherein the antioxidant is dibutylhydroxytoluene.

6. The ointment according to claim 3, wherein the separation inhibitor is polyoxyethylene (196) polyoxypropylene (67) glycol and the antioxidant is dibutylhydroxytoluene.

* * * * *